United States Patent [19]

Hitzman

[11] E Re. 30,965

[45] Reissued Jun. 8, 1982

[54] FERMENTATION OF OXYGENATED HYDROCARBON COMPOUNDS WITH THERMOPHILIC MICROORGANISMS AND MICROORGANISMS THEREFOR

[75] Inventor: Donald O. Hitzman, Bartlesville, Okla.

[73] Assignee: Provesta Corporation, Bartlesville, Okla.

[21] Appl. No.: 938,589

[22] Filed: Aug. 31, 1978

Related U.S. Patent Documents

Reissue of:

[64] Patent No.: 3,981,774
Issued: Sep. 21, 1976
Appl. No.: 618,191
Filed: Sep. 30, 1975

[51] Int. Cl.[3] ..... C12P 21/00

[52] U.S. Cl. ..... 435/68; 435/247; 435/253; 435/804

[58] Field of Search ..... 435/68, 804, 253, 247

[56] References Cited

U.S. PATENT DOCUMENTS

| | | | |
|---|---|---|---|
| 2,983,652 | 5/1961 | Baerfuss | 195/28 R |
| 3,355,296 | 11/1967 | Perkins et al. | 195/28 R |
| 3,462,275 | 8/1969 | Bellamy | 435/804 |
| 3,546,071 | 12/1970 | Dours, Jr. et al. | 195/28 R |
| 3,616,224 | 10/1971 | Shido et al. | 195/49 |
| 3,642,577 | 2/1972 | Gorring | 435/248 |
| 3,642,578 | 2/1972 | Hitzman et al. | 435/68 |
| 3,644,175 | 2/1972 | Dasinger et al. | 195/28 R |
| 3,677,895 | 7/1972 | Hashimoto | 195/28 R |
| 3,681,200 | 8/1972 | Ridgway, Jr. | 195/49 |
| 3,755,082 | 8/1973 | Terul et al. | 195/49 |
| 3,764,476 | 10/1973 | Abe et al. | 195/49 |
| 3,764,481 | 10/1973 | Muller | 195/109 |
| 3,778,349 | 12/1973 | Cartu | 195/33 |
| 3,860,489 | 1/1975 | Cooper | 435/804 |
| 3,891,772 | 6/1975 | Ridgway et al. | 435/804 |

FOREIGN PATENT DOCUMENTS

| | | |
|---|---|---|
| 437120 | 7/1973 | Australia . |
| 2407740 | 8/1974 | Fed. Rep. of Germany . |
| 1231058 | 5/1971 | United Kingdom . |
| 1326582 | 8/1973 | United Kingdom . |
| 1210770 | 10/1970 | United Kingdom . |

OTHER PUBLICATIONS

Applied Microbiology, vol. 27, No. 6, pp. 1112–1117 (1974).
Chemical Engineering, pp. 62–63, Jan. 7, 1974.
Applied Microbiology, vol. 26, No. 6, pp. 982–990 (1973).
Science, vol. 157, pp. 1322–1323 (1967).
Process Biochemistry, pp. 22–24 (6–1973).
Petroleum and Microbiology, Eighth World Petroleum Congress, Moscow, 1971, vol. 5, pp. 149–156.
Mateles et al., Science, vol. 157, pp. 1322 & 1323, Sep. 1967.

*Primary Examiner*—Alvin E. Tanenholtz

[57] ABSTRACT

Single cell protein (SCP) and other fermentation products are produced by aerobic fermentation processes at relatively high temperature conditions employing oxygenated hydrocarbon compounds, such as methanol, as carbon and energy source material, and employing certain unique species Bacillus NRRL B-8066 or NRRL B-8065 as microbial conversion agent, preferably in foam-filled fermentation means.

27 Claims, No Drawings

FERMENTATION OF OXYGENATED HYDROCARBON COMPOUNDS WITH THERMOPHILIC MICROORGANISMS AND MICROORGANISMS THEREFOR

Matter enclosed in heavy brackets [ ] appears in the original patent but forms no part of this reissue specification; matter printed in italics indicates the additions made by reissue.

*This is a reissue application of application Ser. No. 618,191, filed Sept. 30, 1975, now U.S. Patent 3,981,774, patented Sept. 21, 1976.*

FIELD OF THE INVENTION

The invention relates to the production of single cell protein.

BACKGROUND OF THE INVENTION

Efforts to relieve the worldwide shortages of protein have included various biosynthesis processes wherein biologically produced single cell proteins (SCP) are obtained by the growth of a variety of microorganisms on a variety of carbon-containing substrates. The carbon and energy sources used as substrates should be available widely, relatively cheap, uniform, and safe in that they do not leave harmful residues in the protein product ultimately obtained by microbial conversion. Petroleum hydrocarbons have been employed as a carbon and energy source, but have faced practical difficulties in the lack of water solubility, in the high consumption of oxygen to assist in the microbial conversion, and allegedly in traces of potentially carcinogenic agents from the petroleum feedstocks entering or adhering to the protein product.

Other processes have centered on the use of oxygenated hydrocarbon derivatives as feedstocks, due to their water solubility and hence ease of handling since microbial conversion processes are essentially conducted under aqueous conditions. Such feedstocks are readily available either from petroleum sources, natural gas sources, various waste/garbage processing and conversion of methane and the like, from fermentation of various grains and the like, destructive distillation of wood, and so on. Such oxygenated hydrocarbons, whatever their source, are widely available and relatively cheap feedstocks for fermentation processes. Advantages accrue in that these feedstocks are partially oxygenated, so that substantially reduced molecular oxygen requirements are involved for the microbial conversion-growth process.

However, another difficult and limiting factor in the commercialization of the single cell protein processes has been the necessity to function at relatively moderate temperatures of about 20° to 50° C., and more preferably not over about 35° C. The microbial conversion is a highly exothermic oxidation reaction with large quantities of heat being produced, which heat must be removed continuously and consistently or risk the overheating of the system and death of the microorganisms, or at least the severe limitation and growth encountered as temperatures rise, and hence severe reductions in efficiencies.

Many processes have concentrated on employment on one or other of the many available yeasts as the microorganism. Many yeasts are available, and the yeast cells generally are slightly larger than a bacteria cell, and sometimes provide easier separation from the fermentation process.

However, the bacteria offer advantages, since higher crude protein contents of the cell are obtained from bacteria as compared to production obtainable from the yeasts in general, the yeasts having higher proportions of nonprotein structural material in their cells. Bacteria usually have a significantly higher true protein content, frequently being nutritionally higher in the important sulfur amino acids and lysine.

Discovery of bacteria with the capability of rapid growth and high productivity rates at relatively high fermentation process temperatures would be distinctly advantageous. High temperature growth operation means less heat to be removed, less cooling apparatus involved, and ultimately relatively smaller amounts of heat needed for sterilization, coagulation, and separation processes. Danger of contamination with other microbes is also greatly reduced. Thermophilic or thermotolerant bacteria are needed for commercialization of the single cell protein process.

SUMMARY OF THE INVENTION

I have discovered two very unique thermophilic species of bacteria, division Protophyta, class Schizomycetes, order Eubacteriales, family Bacillaceae, genus Bacillus, with highly desirable and useful properties. These unique thermophilic species grow better at higher temperatures than at conventional temperatures.

These two unique species are thermophilic, grow effectively with high productivity on oxygenated hydrocarbon feedstocks, particularly lower alcohols, most preferably methanol or ethanol, at temperatures wherein other known Bacillus species either are relatively unproductive, or simply cannot tolerate, or are unproductive and intolerant of an oxygenated hydrocarbon feedstock. These unique species which I have discovered, and employ in my process, are designated as follows:

| Culture Name | My Strain Designation | Depository Designation |
|---|---|---|
| *Bacillus* sp. | 47 | NRRL B-8065 |
| *Bacillus* sp. | 72 | NRRL B-8066 |

The designations NRRL B-8066 and NRRL B-8065 reflect the fact that I have deposited my thermophilic Bacillus sp. strain 72 and Bacillus sp. strain 47 with the official depository United States Department of Agriculture, Agricultural Research Service, Northern Region Research Laboratory, Peoria, Illinois 61604, by depositing therein thirty lyophilized preparations of each, and have received from the depository the individual NRRL strain designations as indicated. These unique cultures have been deposited in accordance with the procedures of the Department of Agriculture such that progeny of these strains will be available during pendency of this patent application to one determined by the Commissioner of Patents to be entitled thereto according to the Rules of Practice in Patent Cases and 35 U.S.C. 122. The deposit has been made in accordance with the Patent Office practice such that all restrictions on availability to the public of progeny of the unique strains will be irrevocably removed upon granting of a patent of which these important strains are the subject, so that these strains will be available to provide samples for utilization in accordance with my invention.

Thus, culture samples from these deposits or from my cultures from which the deposits were made thus provide strains derived from the thermophilic species of my discovery.

DETAILED DESCRIPTION OF THE INVENTION

I have discovered two strains of peculiarly and uniquely effective thermophilic bacteria of the Bacillus species which I have designated strain 47 and which has received depository designation NRRL B-8065, and strain 72 which has received depository designation NRRL B-8066. The Bacillus strains are highly productive at relatively high fermentation temperatures, producing desirable and valuble single cell protein products with a high protein content of desirable amino acid type and balance. These unique high temperature preferring Bacillus species mean improved rates of single cell protein production, with reduced cooling requirements when grown on a carbon and energy substrate of an oxygenated hydrocarbon, preferably a lower alcohol, more preferably methanol or ethanol, and presently preferred is methanol or a substantially methanol-containing substrate. Further, it is anticipated that these high temperature preferring novel Bacillus species will find particular application in foam-filled fermentation means.

Culture No. 72 NRRL B-8066 is a Bacillus species, gram positive, spore-forming microbe of narrow rod-shaped appearance. No colored pigments have been observed in the cells.

Culture No. 47 NRRL B-8065 is a Bacillus species, gram positive, spore-forming microbe of thick rod-shaped appearance. No colored pigments have been observed in the cells.

The present invention, providing as it does the process for culturing oxygenated hydrocarbon assimilating microbial cells belonging to two new species of microorganisms, is directed toward aerobic culturing in a medium containing oxygenated hydrocarbon as carbon and energy source, at relatively elevated fermentation temperature, resulting in rapid propagation of the cells.

The newly isolated novel and unique microorganisms can be characterized by properties as shown in the following tabulation along with properties of several known Bacillus cultures:

| Culture Property or Test Result | Culture 47 NRRL B-8065 | Culture 72 NRRL B-8066 | Bacillus Cultures *B. licheniformis* NRRL B-1001 | *B. coagulans* NRRL B-1103 | *B. subtilis* ATCC 10774 | *B. stearothermophilis* ATCC 12987 |
|---|---|---|---|---|---|---|
| Gram Staining | Positive | Positive | Positive | Positive | Positive | Variable |
| Spore Forming | Yes | Yes | Yes | Yes | Yes | Yes |
| Aerobic | Yes | Yes | Yes | Yes | Yes | Yes |
| Approx. Size, μ | 0.5 × 1-2.5 | 0.6 × 1-5 | 0.6-0.8 × 1.5-3 | 0.6-2.5 × 1-5 | 0.7-0.8 × 2-3 | 0.6-1 × 2-5 |
| Motility | Yes | Yes | Yes | Yes | Yes | Yes |
| Optimum temp., °C. | 55 | 55 | 32-45 | 33-45 | 28-40 | 30 |
| Max. temp., °C. | 60-65 | 60-65 | 50-56 | 55-60 | 50-55 | 50-55 |
| pH Range | 5-9 | 5-9 | 5.2-8.2 | 5-7 | 5-8.6 | 4.5-6.6 |
| Optimum pH (IM2 medium) | 6.2-6.8 | 6.2-6.5 | NG | NG | NG | NG |
| Growth factors | none required | none required | none required | thiamine, biotin | none required | NG |
| Pigments in IM2 medium + 1.5% $CH_3OH$ | tan . $H_2O$ sol., insol. in organic solvents | yellow. $H_2O$ sol., insol. in organic solvents | NG | NG | NG | NG |
| Cell appearance | rods to long chains | rods | rods, no chains | rods, no chains | rods, no chains | rods, sometimes filamentous |
| Colony appearance on IM2 medium + 1.5% $CH_3OH$ | circular raised, pale tan | circular raised, off white | NG | NG | NG | NG |
| Growth at 55° C. on: | | | | | | |
| Nutrient broth | − | − | + | + | + | + |
| Nutrient broth + 1% $CH_3OH$ | ± | + | + | + | − | + |
| IM2 + 0.5% $CH_3OH$ | + | + | − | − | − | − |
| IM2 + 1.5% $CH_3OH$ | + | + | − | − | − | − |
| Glucose | − | − | + | + | + | + |
| $CH_3OH$ | + | + | − | − | − | − |
| $CH_3CH_2OH$ | + | + | − | − | − | − |
| HCHO | + | + | − | − | − | − |
| BHM + 1.5% $CH_3OH$ + 0.1% NaCl | + | + | − | − | − | − |
| BHM + 5% $CH_3OH$ | + | + | − | − | − | − |
| Plate count + 1.5% $CH_3OH$ | translucent spreading edges | translucent glistening small | − | − | − | − |

+ = visible evidence of growth as determined by increase in turbidity of the starting mixture.
− = not growing; no visible evidence of growth.
± = maintaining itself, but no visible evidence of additional growth.
NG = did not grow on this media.

These comparisons were all made so as to have as direct a comparison between species as possible. Of course, as with all microorganisms, some of the characteristics may be subject to some variation depending on the medium and particular conditions.

The carbon and energy source material or substrate for the fermentation process of my invention employing my novel and unique species of bacteria is a carbon-oxygen-hydrogen-containing water-soluble compound or compounds. The term oxygenated hydrocarbon is designed to be a generic term descriptive of the compounds employable, and not necessarily a limiting term referring to the source of the substrate. The oxygenated hydrocarbons can include alcohols, ketones, esters, ethers, acids, and aldehydes, which are substantially water-soluble in character, and should be limited, because of this characteristic, to up to about 10 carbon atoms per molecule.

Illustrative examples include: methanol, ethanol, propanol, butanol, pentanol, hexanol, 1,7-heptanediol, 2-heptanol, 2-methyl-4-pentanol, pentanoic acid, 2-methylbutanoic acid, 2-pentanol, 2-methyl-4-butanol, 2-methyl-3-butanol, 2-butanol, 2-methyl-1-propanol, 2-methyl-2-propanol, 2-propanol, formic acid, acetic acid, propanoic acid, formaldehyde, acetaldehyde, propanal, butanal, 2-methylpropanal, butanoic acid, 2-methylpropanoic acid, pentanoic acid, glutaric acid, hexanoic acid, 2-methylpentanoic acid, heptanedioic acid, heptanoic acid, 4-heptanone, 2-heptanone, octanoic acid, 2-ethylhexanoic acid, glycerine, ethylene glycol, propylene glycol, 2-propanone, 2-butanone, diethyl ether, methyl ethyl ether, dimethyl ether, di-n-propyl ether, n-propyl isopropyl ether, and the like, including mixtures of any two or more.

A preferred group of such carbon and energy source materials are the water-soluble aliphatic monohydric hydrocarbyl alcohols due to their water solubility, still more preferred are the lower alcohols of 1 to 4 carbon atoms per molecule for commercial availability, still more preferred are ethanol and methanol, presently with methanol being most preferred, due to the low relative cost of these feedstocks.

It is feasible to employ mixtures of any of these oxygenated hydrocarbons if desired or convenient. For example, a commercially available material sometimes termed "methyl fuel" (C. & E. N., Sept. 17, 1973, page 23) is a mixture of methanol and controlled percentages of higher alcohols containing up to 4 carbon atoms per molecule, and is a suitable substrate.

Petroleum gases can be oxidized and employed, such as methane, ethane, and the like, which provide mixtures of predominantly the corresponding alcohol, as well as varieties of ketones, aldehydes, ethers, acids, and the like, and hydrocarbon fractions from various petroleum sources can be utilized for this purpose.

FERMENTATION CONDITIONS

Culturing of my unique and novel species of bacteria with the oxygenated hydrocarbon feedstocks can be advantageously carried out in a temperature range of about 45°-65° C., more preferably about 50° to 60° C., presently most preferred for optimum growth rates about 55° C.

Culturing is accomplished in a growth media comprising an aqueous mineral salt medium, the carbon and energy source material, molecular oxygen, and, of course, starting inoculum of the particular species to be employed.

High concentrations of some of the described carbon and energy substrates, such as methanol, or formaldehyde, or the like, may be inhibitory to satisfactory microbial growth or even toxic to the microorganisms in the fermentations employing the novel Bacillus species. Relatively high concentrations of substrates thus should be avoided, so that it is desirable to maintain the substrate concentration in the fermentation means at a level of about 0.01 to 5 volume/volume percent preferably about 0.01 to 0.5 volume/volume percent so as to neither starve nor inhibit the growth rates.

Oxygen can be supplied to the fermentation media or broth in any form capable of being assimilated readily by the inoculant microorganism. While molecular oxygen supplying compounds can be utilized, these are not normally commercially practical. Thus, molecular oxygen conventionally is supplied as the molecular oxygen-containing gas, such as air at atmospheric or elevated pressure, or oxygen-enriched air where convenient and available from sources depending on particular location of the SCP process operation. In effect, using the oxygenated hydrocarbon substrate, a part of the oxygen needed for growth of the microorganism is supplied by the oxygen content of the substrate. Nevertheless, additional quantities of molecular oxygen must be supplied for growth since the assimilation of the substrate and corresponding growth of the microorganism is, in effect, a combustion process. In general, between about 0.1 and 10, preferably between about 0.7 and 2.5, volumes per minute of air of normal oxygen content are supplied to the reactor per volume of liquid in the fermentor, or in terms of oxygen, the respective ranges would be about 0.02 to 2.1, and 0.14 to 0.55.

The pressure employed for the microbiological conversion process can range widely, and pressures of about 0.1 to 100 atmospheres, preferably 1 to 30 atmospheres, and more preferably slightly over atmospheric pressure, are employed as a balance of equipment cost vs. $O_2$ solubility achieved. Greater than atmospheric pressures are advantageous in that such pressures tend to increase the dissolved oxygen concentration in the aqueous fermentation admixture, which in turn can increase cellular growth rate. Higher than atmospheric pressures are preferred at higher fermentation temperatures where oxygen solubilities tend to decrease. Foam-filled fermentation means tend to assist oxygen transfer necessary for high cell densities and rapid growth rates.

NUTRIENTS

The two unique Bacillus species of my discovery require mineral nutrients and a source of assimilable nitrogen, in addition to the oxygen and carbon and energy sources as described. The source of nitrogen can be any nitrogen-containing compound which is capable of releasing nitrogen in a form suitable for metabolic utilization by the organism. While a variety of organic nitrogen source compounds such as other proteins, urea, or the like can be employed, usually inorganic nitrogen source materials are more economical and practical. Suitable inorganic nitrogen-containing compounds include such as ammonia, ammonium hydroxide, various ammonium salts such as ammonium citrate, ammonium phosphate, ammonium sulfate, ammonium pyrophosphate, or various other individual compounds can be utilized. Ammonia gas is convenient and can be employed by bubbling through the aqueous fermentation media in suitable amounts.

The pH range in the aqueous microbial fermentation admixture should be in the exemplary range of about 5 to 9, more preferably about 6 to 8. The unique microorganisms of my discovery in the process of my invention seem to prefer a pH in the range of about 6 to 7.5. These microorganisms more particularly prefer a pH of about 6.2-6.8 for NRRL B-8065, and 6.2-6.5 for NRRL B-8066, in what I term IM2 media. pH range preferences for microorganisms are dependent on the media employed, and thus change somewhat with change in media.

When the carbon and energy source is or contains an aldehyde, in amounts potentially deleterious to the microorganism, the deleterious aldehyde effects can be avoided by first treating the substrate with a suitable amount of a nitrogen-containing compound, preferably ammonia, ammonium hydroxide, or other ammonium compound, in a ratio of about 0.01 to 10 mol equivalents of said nitrogen-containing compound for each mol of aldehyde. Such a treated substrate then is not only the carbon and energy source but also contains the necessary nitrogen source in whole or part.

In addition to the oxygen, nitrogen, and carbon and energy sources, it is necessary to supply necessary amounts in proper proportions of selected mineral nutrients in the feed media in order to assure proper microorganism growth, and maximize the assimilation of the oxidized hydrocarbon by the cells in the microbial conversion process.

A source of phosphate or other phosphorus, magnesium, calcium, sodium, manganese, molybdenum, copper, ions appear to provide the essential minerals. The recipe shown below can be used to culture the novel Bacillus species of my discovery and invention, though they will grow on other than methanol-containing substrates. The following is given for guidance to those skilled in the art.

Medium IM2 (solid)

| Component | Amount |
|---|---|
| $KH_2PO_4$ | 2.0 g |
| $K_2HPO_4$ | 3.0 g |
| $MgSO_4 \cdot 7H_2O$ | 0.4 g |
| $CaCl_2 \cdot 2H_2O$ | 0.04 g |
| NaCl | 0.1 g |
| $(NH_4)_2SO_4$ | 2.0 g |
| Agar | 15 g |
| Trace mineral solution[a] | 0.5 ml |
| Distilled water | 1,000 ml |
| Sterile methanol[b] to give | 1.5 vol % |

[a]See recipe below.
[b]Added just prior to use.
For a liquid media, simply omit the agar above.

Trace Mineral Solution

| Component | Amount |
|---|---|
| $CuSO_4 \cdot 5H_2O$ | 0.06 g |
| KI | 0.08 g |
| $MnSO_4 \cdot H_2O$ | 0.3 g |
| $Na_2MoO_4 \cdot 2H_2O$ | 0.2 g |
| $H_3BO_3$ | 0.02 g |
| $ZnSO_4 \cdot 7H_2O$ | 2.0 g |
| $FeCl_3 \cdot 6H_2O$ | 4.8 g |
| Distilled water | 1,000 g |
| $H_2SO_4$ (conc.) | 3.0 ml |

Other materials such as yeast extracts, vitamins, biotin, and the like, or other growth factors, can be added typically in the trace amounts known to the fermentation art.

The culturing of my novel Bacillus species according to my invention can be conducted as a batch, though preferably as a continuous process, by methods known in the fermentation arts, but most preferably in a foam-filled fermentation reactor. Certainly, the continuous process possesses a number of advantages in terms of commercial operations for the production of large quantities of microbial cells, and thus is a preferred mode of performing my invention.

In either a batch, or the preferred continuous operation, all equipment, reactor, or fermentation means, vessel or container, piping, attendant circulating or cooling devices, and the like, are sterilized, usually by employing steam such as at about 250° F. for several minutes, such as about 15 minutes. The sterilized reactor is inoculated with a culture of the specified microorganism in the presence of all the required nutrients, and including the oxygen, and the oxygenated hydrocarbon feed.

In continuous process, as the culture begins to grow, the continuous introduction of air, nutrient medium, nitrogen source if added separately, and oxygenated feedstock such as alcohol, is maintained. The addition rate of the various streams can be varied so as to obtain as rapid a cell growth as possible consistent with the efficient utilization of the oxygenated hydrocarbon input, so that the objective of a maximized high yield of cell weight per weight of carbon and energy source material charged is obtained. The feed rate of the carbon and energy source material should be adjusted so that the amounts being fed to the fermenter is substantially the same as the rate of consumption by the organism to avoid overfeeding, particularly of toxic materials, such as an alcohol or aldehyde, which might inhibit the growth or even kill the microorganisms. A satisfactory condition usually is exhibited by there being little or no carbon and energy source material in the effluent being withdrawn from the fermenter, though a satisfactory check can be obtained by watching the carbon and energy source material content of the fermenter effluent and maintaining it at a desirable low level such as about 0.1 to 0.5 volume/volume percent. Of course, any of the feed streams can be added either incrementally or continuously as desired or convenient.

Instrumentation should be maintained to measure cell density, pH, dissolved oxygen content, alcohol or other feedstock concentration in the fermenter, temperature, feed rates of input and output streams, and the like. It is preferred that materials fed to the fermenter be sterilized prior to introduction into the fermenter. Where the oxygenated hydrocarbon feedstock is a material capable of sterilizing other materials, such as the methanol, ethanol, or formaldehyde, in some instances, it may be convenient to add this component to other streams, such as the mineral media, in sterilizing amounts, and thus accomplish several purposes without the necessity for a separate sterilization of the mineral media such as by heat and the like.

The type of fermenter employed is not critical in the practice of the fermentation process of my invention employing the species of my discovery, though presently preferred is operation in a foam-filled fermenter. High productivity of pure cultures of my unique thermophiles with oxygenated hydrocarbon feed is best achieved in a continuous process when the process occurs in a foam-filled system. The pure cultures at my recommended fermentation temperatures achieve high growth rates and cause a very stable foam to be produced. Of course, watch must be maintained to control growth rates to avoid foam out of the fermenter which could lower the liquid volume and cause some loss of the fermenter contents. Addition of antifoam is to be avoided, if at all possible, since antifoams such as the silicones may be detrimental to the dissolved oxygen content at the recommended high temperatures, and may cause the organism to grow at a slower rate, cut productivity, or even to die. The foam produced with my species is not harmful to growth and is definitely beneficial in maintaining the organisms in a system of high dissolved oxygen. The encouragement of such foam process in a fermenter designed to encourage and maintain the produced foam is beneficial to the process of achieving the increased $O_2$ transfer necessary to maintain the high cell density and rapid growth rate which these thermophilic organisms require. The process of using a foam-filled fermenter with my unique oxygenated hydrocarbon-consuming thermophiles which produce substantial foam results in the SCP being most efficiently produced.

Foam-filled operation of the fermenter is particularly suited for carrying out fermentation processes in which large quantities of gases are to be maintained in intimate contact with the liquid phase, so as to obtain a reaction along relatively large areas of contacting interface. Thus, fermentation is improved, and heat transfer is improved as to control, uniformity, and avoidance of hot spots.

One presently preferred type of fermenter can be observed in FIG. 1 on page 37 of Process Biochemistry, June, 1972, to which can be added a conduit for introducing a molecular oxygen-containing gas into the vessel at any convenient point, preferably within the draft tube and just above the mixing device since the aspirating action of the mixing device then can be advantageously employed in aiding the introduction of air into the contents of the vessel. This type of fermenter operates efficiently with its contents substantially completely converted to a foam or low density emulsion with very high consequent oxygen transfer rates being achieved.

Another type of fermenter that can be employed is the airlift fermenter which is described in the article by Wang et al. in the Proceedings Eighth World Petroleum Congress, Vol. 5, pp. 149–156 (1971) published by Applied Science Publishers Ltd., London, England.

Still another type fermenter that can be utilized is the pressure cycle fermenter which is described on page 63 of Chemical Engineering, Jan. 7, 1974.

Finally, another type of fermenter which is suitable is the well known tank equipped with a blade stirrer and a submerged aeration device. One fermenter of this type is shown in U.S. Pat. No. 2,983,652.

Where a foam-filled fermentation mode is not employed, it may be necessary to use an antifoam agent in carrying out the fermentation process of the instant invention. Suitable antifoam agents and methods of applying the same are well known in the fermentation art, though such mode is much less preferred with my unique species.

PRODUCT RECOVERY

Both the cellular and extracellular products of culturing the novel Bacillus species on the substrates according to my process can be recovered by conventional means. The cells can be separated from the fermenter effluent by centrifugation, filtration or the like. The cell-free effluent can then be treated with acetone or a lower alcohol such as methanol or ethanol to precipitate any polymeric material produced extracellularly. The cell-free effluent also can be treated by solvent extraction and/or base extraction to recover if desired other extracellular products such as pigments, vitamins or organic acids produced during the culturing process. The microbial cells usually are killed by heat or chemical means and this can be done before or after separation of the cells from the fermenter effluent. The bacterial cells are a valuable source of protein for man as well as animals. For human consumption the cells can be treated to reduce the nucleic acid content, but for animal feed purposes such treatment does not appear necessary.

EXAMPLES

The following examples are descriptive of runs employing the novel species of my discovery. Particular amounts of materials, or particular types of oxygenated hydrocarbon-containing feedstocks employed should be considered as illustrative and not as limitative of my invention.

EXAMPLE I

Several cultures of known thermophilic microorganisms were obtained from two culture depositories. The United States Department of Agriculture, Northern Regional Research Laboratories, Peoria, Illinois, and The American Type Culture Collection ATCC, Washington, D.C. These cultures were received in lyophilized condition. The cultures were tested for growth at 55° C. in a variety of different media. The results of these tests are shown in Table I below. The cultures employed were as follows:

| Species | Deposit No. |
|---|---|
| *Bacillus subtilis* | ATCC 10774 |
| *Bacillus stearothermophilis* | ATCC 12987 |
| *Bacillus stearothermophilis* | NRRL B1102 |
| *Bacillus coagulans* | NRRL B1103 |
| *Bacillus coagulans* | NRRL B1168 |
| *Bacillus licheniformis* | NRRL B1001 |

TABLE I

| Culture No. | Growth + or − in Medium No. 1[a] | 2[b] | 3[c] | 4[d] | 5[e] |
|---|---|---|---|---|---|
| NRRL B1001 | + | + | + | + | − |
| NRRL B1103 | + | + | + | + | − |
| ATCC 12987 | + | + | + | + | − |
| NRRL B1168 | + | + | + | + | − |
| NRRL B1102 | − | | | | |
| ATCC 10774 | + | − | − | − | |

[a]Nutrient Broth (NB)
[b]NB + 1% methanol
[c]NB (½ strength) + 1% methanol
[d]NB (¼ strength) + 1% methanol
[e]IM2 medium + 0.5% methanol The nutrient broth used above is a conventional culture medium having 3 g/l of beef extract and 5 g/l of peptone. Medium IM2 is the medium as described hereinbefore except for the absence of agar in these runs using liquid media. NRRL B1102 would not grow even on nutrient broth. ATCC 10744 would not grow in the presence of methanol (Medium 2). Although the other cultures would grow in the presence of methanol, they evidently were unable to utilize methanol as the sole source of carbon and energy for their growth. These results are in dramatic contrast to the desirable results obtained with my unique Bacillus species employed in the process of my invention since my unique Bacillus species were able to efficiently utilize methanol as their sole carbon and energy source.

EXAMPLE II

A continuous fermentation run was carried out according to the process of my invention. The inoculum for the run was 500 ml of an aqueous dispersion of cells of Culture No. 72, NRRL B-8066, which had been grown for 24 hours on the medium BH-M with 1.5% by volume methanol:

| Medium BH-M | |
|---|---|
| Component | Amount |
| $KH_2PO_4$ | 2.0 g/l |
| $K_2HPO_4$ | 3.0 g/l |
| $MgSO_4 . 7H_2O$ | 0.4 g/l |
| $CaCl_2 . 2H_2O$ | 0.04 g/l |
| $(NH_4)_2SO_4$ | 2 g/l |
| Trace mineral solution* | 10 ml/l |

*The trace mineral solution was composed of the following materials:

| Component | Amount |
|---|---|
| $FeSO_4 . 7H_2O$ | 0.11 g/l |
| $ZnSO_4 . 7H_2O$ | 0.03 g/l |
| $CuSO_4 . 5H_2O$ | 0.02 g/l |
| $MnSO_4 . H_2O$ | 0.02 g/l |
| $H_2SO_4$ (conc.) | 1 ml/l |

The inoculum described above was added to a fermenter equipped with stirring and aeration means and having therein two liters of the medium made with tap water described below:

| FM-12 Medium | |
|---|---|
| Component | Amount |
| $H_3PO_4$ (85%) | 2.0 ml |
| KCl | 1.0 g |
| $MgSO_4 . 7H_2O$ | 1.5 g |
| $CaCl_2 . 2H_2O$ | 0.2 g |
| NaCl | 0.1 g |
| Trace Mineral Solution* | 10.0 ml |
| Distilled Water | To make 1 liter |

*This trace mineral solution was formulated as given in the recipe shown below:

| Trace Mineral Solution | |
|---|---|
| Component | Amount, g |
| $CuSO_4 . 5H_2O$ | 0.06 |
| KI | 0.08 |
| $FeCl_3 . 6H_2O$ | 4.80 |
| $MnSO_4 . H_2O$ | 0.30 |
| $Na_2MoO_4 . 2H_2O$ | 0.20 |
| $ZnSO_4 . 7H_2O$ | 2.00 |
| $H_3BO_3$ | 0.02 |
| $H_2SO_4$ (conc.) | 3 ml |
| Distilled water | To make 1 liter |

The methanol content was initially 1.5% (v/v), pH was about 6.7, and temperature was about 55° C. Stirring rate of the contents was at about 1000 rpm, and air was introduced at about 2 liters per minute. Ammonium hydroxide was added continuously to keep the pH in the range of about 6.7–6.9 and also to provide a source of nitrogen.

After good growth of the inoculum was observed, a continuous addition of the nutrient medium having 5% by volume methanol was started and a corresponding volume of fermenter effluent was withdrawn. The feed rate for the nutrient mixture varied from about 150 to 800 ml/hour during the course of the run of about 500 hours. The average retention time for cells in the fermenter varied from about 2.4 to 5 hours. The fermenter effluent was sampled from time to time so as to recover some of the cells, which were dried, weighed, and subjected to protein analysis. The affluent samples were processed to recover only cells, i.e., solubles were not analyzed. Cell concentration values ranged from about 12 g/l (dry cells) early in the run (25 hours), to 18 g/l at 190 hours and about 24 g/l near the end of the run. Methanol conversion to recoverable cells was 44% of that charged. The protein content for a sample of cells taken during the course of this run has been presented hereinabove in the discussion describing product recovery.

The results above show that the novel Bacillus species NRRL B-8066 of this invention could be readily cultured continuously at 55° C. with methanol as the source of energy and carbon. Furthermore, the cells of this species have been shown to be high in protein content.

EXAMPLE III

Another continuous fermenter run was carried out using the culture NRRL B-8066 of Example II. In this run the fermenter was inoculated with 500 ml of an aqueous dispersion of the culture which had been grown for 26 hours on IM2 medium plus 1.5% by volume methanol:

| IM2 Medium | |
|---|---|
| Component | Amount |
| $KH_2PO_4$ | 2.0 g/l |
| $K_2HPO_4$ | 3.0 g/l |
| $MgSO_4 . 7H_2O$ | 0.4 g/l |
| $CaCl_2 . 2H_2O$ | 0.04 g/l |
| NaCl | 0.1 g/l |
| $(NH_4)_2SO_4$ | 2.0 g/l |
| *Trace mineral solution | 0.5 ml/l |

*The trace mineral solution was composed of the following materials for one liter aqueous solution:

| Trace Mineral Solution | |
|---|---|
| Component | Amount |
| $CuSO_4 . 5H_2O$ | 0.06 g |
| KI | 0.08 g |
| $FeCl_3 . 6H_2O$ | 4.80 g |
| $MnSO_4 . H_2O$ | 0.30 g |
| $Na_2MoO_4 . 2H_2O$ | 0.20 g |
| $ZnSO_4 . 7H_2O$ | 2.00 g |
| $H_3BO_3$ | 0.02 g |
| $H_2SO_4$ (conc.) | 3 ml |

The inoculum described above was added to a fermenter of the same type as described in Example II. The fermenter contained two liters of the same medium, FM-12, described in the fermentation run of Example II except that only 5 ml per liter of the above trace mineral solution was added to the medium.

The methanol content was initially limited to about 1.5% v/v, pH was about 7.1, and the temperature was about 53° C. During the first two hours, stirring and air volumes were increased slowly up to 800 rpm and 2 liters per minute, respectively. Ammonium hydroxide was added as described in Example II to keep the pH in the range of about 7.0–7.2, and as well to provide a source of nitrogen.

After good growth of the inoculum was established during the first 24 hours, the continuous addition of the nutrient medium having 7.5% by volume methanol and 0.05 g/l $MnSO_4.H_2O$ was started and a corresponding volume of fermenter effluent was withdrawn. The feed rate for the nutrient medium mixture was about 200 to 400 ml/hour during the course of the run of about 94 hours. Average retention time in the fermenter varied from about 3 to 5 hours. The fermenter effluent was sampled from time to time to recover and dry the cells which were weighed. The effluent samples were processed to recover only the cells, i.e., solubles were not analyzed. Cell concentrations after 24 hours ranged from 17 to 26 g/l (dry cells). Methanol conversion to recoverable cells was about 43% of that charged.

The above results demonstrate again a good yield of microbial cells from the novel Bacillus species can be obtained by using methanol as the sole source of energy and carbon at a high fermentation temperature.

EXAMPLE IV

A continuous fermentation run was conducted with Culture 47 NRRL B-8065.

A fermenter was used of the same type as previously described. The fermenter contained two liters of the FM-12 medium as described in Example III, but in this instance made up with deionized water, was charged with 500 ml of an aqueous dispersion of Culture 47 NRRL B-8065 grown for 11 hours on the same inoculum IM2 medium as described in Example III with 1.5% by volume methanol.

The methanol content was initially 1.5% (v/v), pH initially was about 6.45, and the temperature was maintained at about 54° C. As in Examples II and III, ammonium hydroxide was added to keep the pH at about 6.3–6.6 and as well to provide a source of nitrogen. Stirring and air volume rate were gradually increased to 400 rpm and 0.5 liter per minute respectively over a period of about 7 hours. After about 11 hours the continuous addition of nutrient medium, FM-12 made with tap water, having 2.5% by volume methanol and additionally 1 g/l $KH_2PO_4$, 1 g/l $K_2HPO_4$ and a small amount of antifoam agent was started. After 28 hours the feed was modified by providing additional $MnSO_4 \cdot H_2O$ to double its concentration in the feed. This adjustment appeared to stimulate to some extent oxygen uptake by the cells. These unique species appear to have a relatively high $Mn^{++}$ requirement for optimum growth.

During the course of the 101.5 hour run, additional amounts of the other trace minerals were added but none seemed to have a stimulatory effect on cell growth rate. In addition to air, the fermenter also was charged after 28 hours with oxygen at an increasing rate of 0.12 up to 0.4 liters per minute. The stirring rate was correspondingly increased from 400 to 800 rpm during this period. The effluent was sampled from time to time to recover the cells, dry, and weigh them.

The feed rate of the media ranged from about 300 ml/hr at 28 hours to about 850 ml/hr at 71 hours to 1070 ml/hr at 95 hours. The residence time for the cells ranged from about 1.8 to 2.5 hours during the last 30 hours. Cell concentrations ranged from about 7 to 10 g/liter (dry cells), and methanol conversion to recoverable cells was about 50% of that charged.

The above results demonstrate that Culture No. 47 NRRL B-8065 also provides a good yield of microbial cells when grown on methanol as the sole source of carbon and energy at relatively high fermentation temperatures.

EXAMPLE V

The crude protein content of the cells of the novel Bacillus species of my discovery is in the range of about 70 to 85% by weight. The crude protein value is obtained by multiplying the weight percent N (Kheldahl analysis) of the dried cells by the factor 6.25. Subjection of these dried cells to a hydrolysis step followed by analysis of the amino acids by gas chromatography shows the protein content to be in the range of about 55 to 70% by weight. An amino acid distribution for one sample of bacterial cells prepared according to my invention using Culture No. 72 NRRL B-8066 is shown below:

| Essential Amino Acid | g/100 g dried cells |
|---|---|
| leucine | 5.52 |
| isoleucine | 4.68 |
| lysine | 5.36 |
| methionine | 1.38 |
| cystine | 0.05 |
| threonine | 2.93 |
| phenylalanine | 2.72 |
| tyrosine | 2.00 |
| tryptophan | 0.79 |
| valine | 5.25 |
| **Nonessential Amino Acid** | **g/100 g dried cells** |
| alanine | 5.83 |
| arginine | 2.93 |
| aspartic acid | 6.38 |
| glycine | 3.76 |
| glutamic acid | 9.95 |
| histidine | 1.18 |
| proline | 2.37 |
| serine | 1.96 |
| Total | 65.04 |
| Total Essential Amino Acids | 30.68 |

It can be noted that the content of sulfur-containing amino acids, e.g., cystine and methionine, is relatively low. In fact, some samples of cells from the above Bacillus species have shown 0.00 g of cystine per 100 g of dried cells. This situation is not unusual in single cell protein SCP processes and can be adjusted by simply adding suitable amounts of synthetic cystine or methionine to the feed ration employing such SCP.

The disclosure, including data, illustrate the value and effectiveness of my invention. The examples, the knowledge and background of the field of the invention, and general principles of microbiology, chemistry, and other applicable sciences, have formed the bases from which the broad descriptions of my invention, including the ranges of conditions and generic groups of operant components have been developed, and which have formed the bases for my claims here appended.

What is claimed is:

1. A method of producing a single cell protein material which comprises culturing a Bacillus microorganism species NRRL B-8066 or NRRL B-8065 in an aqueous medium employing an oxygenated hydrocarbon as carbon and energy source under aerobic fermentation conditions and recovering the resulting microorganisms as a single cell protein material.

2. A process for the production of microbial cells which comprises aerobically culturing under thermophilic fermentation conditions a strain of Bacillus species derived from NRRL B-8065 or NRRL B-8066 in a culture medium containing an oxygenated hydrocarbon as the main carbon and energy source, nutrients, and a nitrogen source.

3. The process of claim 2 further comprising the further step of separating and recovering said microbial cells so produced from said culture medium.

4. The process of claim 3 wherein said strain is derived from said NRRL B-8065.

5. The process according to claim 3 wherein said strain is derived from said NRRL B-8066.

6. The process of claim 2 wherein said process of culturing is conducted at a fermentation temperature in the range of about 45° to 65° C.

7. The process according to claim 6 wherein said oxygenated hydrocarbon carbon and energy source material comprises one or more alcohols, ketones, esters, ethers, acids, or aldehydes, characterized as substantially water-soluble in character, and of up to about 10 carbon atoms per molecule.

8. The process according to claim 7 wherein said oxygenated hydrocarbon is selected from the group consisting of methanol, ethanol, propanol, butanol, pentanol, hexanol, 1,7-heptanediol, 2-heptanol, 2-methyl-4-pentanol, pentanoic acid, 2-methylbutanoic acid, 2-pentanol, 2-methyl-4-butanol, 2-methyl-3-butanol, 2-butanol, 2-methyl-1-propanol, 2-methyl-2-propanol, 2-propanol, formic acid, acetic acid, propanoic acid, formaldehyde, acetaldehyde, propanal, butanal, 2-methylpropanal, butanoic acid, 2-methylpropanoic acid, pentanoic acid, glutaric acid, hexanoic acid, 2-methylpentanoic acid, heptanedioic acid, heptanoic acid, 4-heptanone, 2-heptanone, octanoic acid, 2-ethylhexanoic acid, glycerine, ethylene glycol, propylene glycol, 2-propanone, 2-butanone, diethyl ether, methyl ethyl ether, dimethyl ether, di-n-propyl ether, n-propyl isopropyl ether, or mixture.

9. The process according to claim 7 wherein said carbon and energy source material comprises a water-soluble aliphatic monohydric hydrocarbyl alcohol.

10. The process according to claim 9 wherein said alcohol contains 1 to 4 carbon atoms per molecule.

11. The process according to claim 10 wherein said alcohol is ethanol or methanol.

12. The process according to claim 11 wherein said culturing is conducted at a fermentation temperature in the range of about 50° to 60° C.

13. The process according to claim 12 wherein said carbon and energy source material is maintained at a concentration of about 0.01 to 5 volume/volume percent in said culture medium.

14. The process according to claim 13 wherein said concentration is in the range of about 0.01 to 0.5 volume/volume percent.

15. The process according to claim 13 wherein said aerobic culturing of said strain includes fermentation conditions employing about 0.02 to 2.1 volumes of oxygen per minute per volume of liquid in said culture medium, and wherein said culture medium is maintained under a pressure of about 0.1 to 100 atmospheres and a pH in the range of about 5 to 9.

16. The process according to claim 15 wherein said oxygen is supplied at least in part as air.

17. The process according to claim 9 wherein said oxygenated hydrocarbon carbon and energy source material contains aldehyde, and wherein said aldehyde containing oxygenated hydrocarbon carbon and energy source material is treated with ammonia or an ammonium compound in a ratio of about 0.01 to 10 mol equivalents per mol of aldehyde prior to employing said carbon and energy source material in said culture medium.

18. The process according to claim 15 wherein said culture medium is treated with a manganous compound during said culturing.

19. The process of claim 15 wherein said culturing is conducted in a substantially foam-filled fermentation means under foam-filled fermentation conditions.

20. The process according to claim 15 wherein said microorganism is said NRRL B-8065 species, said carbon energy source material comprises methanol, said fermentation is conducted at a pH in the range of about 6.2–6.8.

21. The process according to claim 15 wherein said microorganism is said NRRL B-8066 species, said carbon energy source material comprises methanol, said fermentation is conducted at a pH in the range of about 6.2–6.5.

22. The process according to claim 15 wherein said strain is said NRRL B-8066, culturing is conducted at a pH in the range of about 6.7–6.9, said culturing or fermentation temperature is about 55° C., ammonium hydroxide is employed as nitrogen source.

23. The process according to claim 15 wherein said strain is said NRRL B-8066, fermentation pH in said culture medium is maintained in the range of about 7–7.2 employing ammonium hydroxide for pH control and as nitrogen source, and said culturing fermentation temperature was about 53° C., and said carbon energy source material is methanol.

24. The process according to claim 15 wherein said Bacillus species is said NRRL B-8065 species, the carbon and energy source substrate is methanol, said fermentation temperature was about 54° C., culture medium fermentation condition pH was in the range of about 6.3–6.6, and ammonium hydoxide is nitrogen source.

*25. A biologically pure culture of bacteria having the identifying characteristics of Bacillus NRRL B-8065 or NRRL B-8066, said culture being capable of producing recoverable amounts of single cell protein upon aerobic fermentation in an aqueous nutrient medium containing assimilable amounts of carbon, nitrogen, and inorganic nutrients, wherein said carbon is substantially supplied in the form of an oxygenated hydrocarbon compound.*

*26. The biologically pure culture of bacteria according to claim 25 wherein said Bacillus is NRRL B-8065.*

*27. The biologically pure culture of bacteria according to claim 25 wherein said Bacillus is NRRL B-8066.*

* * * * *